United States Patent [19]

Wilson et al.

[11] Patent Number: 5,792,450
[45] Date of Patent: Aug. 11, 1998

[54] PURIFIED HUMAN CSF-1

[75] Inventors: Kenneth J. Wilson, Los Altos, Calif.; E. Richard Stanley, New York, N.Y.; Albert Boosman, Pleasant Hill, Calif.; Mary Kim Warren, Boyds, Md.; James E. Strickler, Havertown, Pa.; Judit Csejtey, Walnut Creek, Calif.

[73] Assignees: Chiron Corporation, Emeryville, Calif.; Albert Einstein College of Medicine, New York, N.Y.

[21] Appl. No.: 405,913

[22] Filed: Mar. 13, 1995

Related U.S. Application Data

[63] Continuation of Ser. No. 913,266, Jul. 14, 1992, abandoned, which is a continuation of Ser. No. 607,230, Oct. 31, 1990, abandoned, which is a continuation of Ser. No. 286,304, Dec. 16, 1988, abandoned, which is a continuation of Ser. No. 2,400, filed as PCT/US86/00251 Feb. 5, 1986, abandoned, which is a continuation-in-part of Ser. No. 698,358, Feb. 5, 1985, abandoned.

[51] Int. Cl.$^6$ .................... A61K 38/19; C07K 14/535
[52] U.S. Cl. .................... 424/85.1; 530/351; 530/395; 514/2; 514/8; 930/145
[58] Field of Search .................... 530/351, 395; 574/2, 8; 424/85.1; 930/145

[56] References Cited

U.S. PATENT DOCUMENTS

| | | | |
|---|---|---|---|
| 4,230,697 | 10/1980 | Nishida et al. | 424/177 |
| 4,275,056 | 6/1981 | Takaku | 424/99 |
| 4,289,690 | 9/1981 | Pestka et al. | 530/836 |
| 4,342,828 | 8/1982 | Takaku et al. | 435/41 |
| 4,432,895 | 2/1984 | Tarnowski | 424/85 |
| 4,438,032 | 3/1984 | Golde et al. | 424/85 |
| 4,482,485 | 11/1984 | Funakoshi et al. | 260/112 |
| 4,485,017 | 11/1984 | Tan et al. | 424/85 |
| 4,504,586 | 3/1985 | Nicholson | 436/518 |
| 4,511,503 | 4/1985 | Olson et al. | 424/85 |
| 4,512,922 | 4/1985 | Jone et al. | 424/85 |
| 4,620,948 | 11/1986 | Builder et al. | 530/419 |
| 4,656,255 | 4/1987 | Seely | 530/412 |
| 4,658,018 | 4/1987 | Urdal et al. | 530/531 |
| 4,677,196 | 6/1987 | Rausch et al. | 530/412 |
| 4,847,201 | 7/1989 | Kawasaki et al. | 435/70 |
| 5,422,105 | 6/1995 | Ralph et al. | 424/85.1 |

FOREIGN PATENT DOCUMENTS

| | | |
|---|---|---|
| 1695661 | 1/1986 | European Pat. Off. |
| 0208539 | 1/1987 | European Pat. Off. |
| 0225156 | 10/1987 | European Pat. Off. |
| 2134528 | 8/1984 | United Kingdom |
| 8505637 | 12/1985 | WIPO |
| 8604607 | 8/1986 | WIPO |
| WO8604587 | 8/1986 | WIPO |

OTHER PUBLICATIONS

Waheed et al., Exp. Hemat vol. 12, p. 434 (1984).
Lampson, Monoclonal Antibodies, Kennett et al.(ed.). Plenum Press–New York and London pp. 395–397 (1981).
Ben–Avram et al., 1985, "Correction" *Proc. Natl. Acad. Sci. USA* 82:7801.
Shadduck et al., 1980, *Proc. Soc. Exp. Biol. Med.* 164:40–50.
Abboud et al., 1981, Blood 58:1148, 1150, 1152 and 1154.
Das et al., *J. Biol. Chem.* 257: 13679–13684 (1982).
Das et al., *Blood* 58: (3) 630–641 (1981).
Dexter *Nature* 309:746–747 (1984).
Kriegler et al., *Exp. Hematol.* 12:844–849 (1984).
Ladner et al., *EMBO J.* 6(6) :2693–2698 (1987).
Light, *Biothechniques* 3(4) :298–307 (1985).
Ralph et al., *Immunol.* 172:194–204 (1986).
Rudinger, *Peptide Hormones* University Park Press (1976).
Stanley, *J. Bio. Chem.* 252:4305–4312 (1977).
Strickler et al., *Lymphokine Res.* 3(4) :259 (1984).
Vadas et al., *J. Immunol.* 130 (2):795–799 (1983).
Warren et al., *J. Immunol.* 137:2281–2285 (1986).
Warren et al., *J. Immunol.* 134:982–989 (1985).
Wong et al., *Science* 235:1504–1508 (1987).
Ben–Avram et al., *Proc. Natl. Acad. Sci.* 82:4486–4489 (1985).
Gough et al *Nature* 309:763–767.
Kawasaki et al., *Science* 230:291–296 (1985).
Stanley, *Methods in Enzymology* 116:564–587 (1985).
Waheed et al., *Blood* 60(1) :238–244.
Wang et al., *J. Cellular Biochem.* 21:263–275 (1983).
Stanley et al., "Factor Regulating Macrophage Production and Growth: Idenitity of Colony–Stimulating Factor and Macrophage Growth Factor", *J. Exp. Med.*, 143:631–647 (1976).
Stanley et al., "Standard bioassay for bone marrow colony stimulating factor in human urine: Levels in normal man", *J. Lab. Clin. Med.*, 79:657–668 (1972).
Stricker et al., "Characterization of Human Urinary and Mouse L–Cell CSF–1", *Lymphokines Res.*, 3:259 (1984).
Waheed and Shadduck, "Purification and properties of L cell–derived colony–stimulating factor", *J. Lab. Clin. Med.*, 94(1):180–194 (1979).
Abboud et al., Hydrophobic Adsorption Chromatograpy of Colony–Stimulating Activities and Erthyroid–Enhancin Activity From the Human Monocyte–Like Cell Line, GCT, *Blood*, 58(6):1148–1154 (Dec. 1981).
Hatake et al., "Purification of human urinary colony–stimulating factor by high–performance liquid chromatography", *J. Chrom.*, 344:339–344 (1985).
Metcalf, "The Granulocyte–Macrophage Colony–Stimulating Factors", *Scienc*, 229:16–22 (Jul. 5, 1985).

(List continued on next page.)

*Primary Examiner*—John Ulm
*Assistant Examiner*—Prema Mertz
*Attorney, Agent, or Firm*—Marshall, O'Toole et al.; Robert P. Blackburn

[57] ABSTRACT

The present invention relates to the purification of proteins, to the products of such purification, and to DNA probes constructed therefrom. More specifically, the invention relates to the purification and sequencing of murine and human colony stimulating factor-1 (CSF-1).

3 Claims, 3 Drawing Sheets

OTHER PUBLICATIONS

Motoyoshi, "Purification and Some Properties of Colony-stimulating Factor From Normal Human Urine", *Blood*, 52(5):1012–1020 (Nov. 1978).

Ralph et al., "Biological Properties and Molecular Biology of the Human Macrophage Growth Factor, CSF–1", *Immunobiol.*, 172:194–204 (1986).

Ralph et al., "Distinct Signals for Antibody–Dependent and Nonspecific Killing of Tumor Targets Mediated by Macrophages", *J. Immunol.*, 129(1):427–432 (Jul. 1982).

Shadduck et al., "A Method for the Removal of Endotoxin from Purified Colony–Stimulating Factor (40821)", *Proc. Soc. Exp. Biol. Med.*, 164:40–50 (1980).

Ben–Avram et al., "Amino–terminal amino acid sequence of murine colony–stimulating factor 1", *PNAS (USA)*, 82:4486 (1985).

Burgess et al., "Purification and Properties of Colony–stimulating Factor from Mouse Lung–conditioned Medium", *J. Biol. Chem.* 252:1998 (1977).

Byrne et al., "Distribution of Cells Bearing Receptors for a Colony–stimulating Factor (CSF–1) in Murine Tissues", *Cell Biol.*, 91:848 (1981).

Cantrell et al., "Cloning, sequence, and expression of a human granulocyte/macrophage colony–stimulating factor", *PNAS (USA)*, 82:6250 (1985).

Das et al., "Human–Colony–Stimulating Factor (CSF–1) Radioimmunoassay: Resolution of Three Subclasses of Human Colony–Stimulating Factors", *Blood*, 58:630 (1981).

Das et al., "Structure–Function Studies of a Colony Stimulating Factor (CSF–1)", *J. Biol. Chem.* 257:13679 (1982).

Dexter, "The message in the medium", *Nature*, 309:746 (1984).

Fleit et al., "Interferon Induction in Marrow–Derived Macrophages: Regulation by L Cell Conditioned Medium", *J. Cell Physiol.*, 108:347 (1981).

Fojo et al., "Purification and Characterization of a Colony Stimulating Factor from Human Lung", *Biochemistry*, 17:3109 (1978).

Fung et al., "Molecular cloning of cDNA for murine interleukin–3", *Nature*, 307:233 (1984).

Gough et al., "Molecular cloning of cDNA encoding a murine haematopoietic growth regulator, granulocyte–macrophage colony stimulating factor", *Nature*, 309:763 (1984).

Kawasaki et al. "Molecular Cloning of a complementary DNA encoding human macrophage–specific colony stimulating factor (CSF–1)", *Science* 230:291 (1985).

Lee et al., "Isolation of cDNA for a human granulocyte–macrophage colony–stimulating factor by functional expression in mammalian cells", *PNAS (USA)*, 82:4360 (1985).

Lusis et al., "Purification and Characterization of a Human T–Lymphocyte–Derived Granulocyte–Macrophage Colony–Stimulating Factor", *Blood*, 57:13 (1981).

McCormick et al., "Inducible Expression of Amplified Human Beta Interferon Genes in CHO Cells", *Mol. Cell. Biol.*, 4:166 (1984).

Metcalf, "Studies on Colony Formation In vitro by Mouse Bone Marrow Cells", *J. Cell Physiol.*, 76:89 (1970).

Moore et al., "Enhanced Responsiveness of Committed Macrophage Precursors to Macrophage–Type Colony–Stimulating Factor (CSF–1) Induced In Vitro by Interferons $\alpha$ & $\beta$", *J. Immunol.*, 131:2374 (1983).

Moore et al., "Endogenous Regulation of Macrophage Proliferative Expansion by Colony–Stimulating Factor–Induced Interferon", *Science*, 223:178 (1984).

Nozawa et al., "Stimulation by Conditioned Medium of L–929 Fibroblasts, E. coli Lipopolysaccharide, and Muramyl Dipeptide of Candidacidal Activity of Mouse Macrophages", *Cell Immunol.*, 53:116 (1980).

Prystowsky et al., "A Microassay for Colony–Stimulating Factor Based on Thymidine Incorporation", *Am. J. Pathol.*, 114:149 (1984).

Ralph et al., "Colony–Stimulating Factors and Regulation of Macrophage Tumoricdal and Microbicidal Activities", *Cell Immunol.*, 76:10 (1983).

Stanley et al., "Factors Regulating Macrophage Production and Growth", *J. Biol. Chem.*, 252:4305 (1977).

Stanley, "Colony Stimulating Factors", *The Lymphokines*, Stewart, W.E. II et al. (eds) Humana Press, Clifton NJ pp. 102–132 (1981).

Stanley, "The Macrophage Colony–Stimulating Factor, CSF–1", *Meth. Enzymol.*, 116:564 (1985).

Stanley et al., "Methods For The Purification, Assay, Characterization And Target Cell Binding Of A Colony Stimulating Factor (CSF–1)", *J. Immunol. Meth.*, 42:253 (1981).

Vadas et al., "Activation of Antibody–Dependent Cell–Mediated Cytotoxicity Of Human Neutrophils and Eosinophils By Separate Colony–Stimulating Factors", *J. Immunol.*, 130:795 (1983).

Waheed et al., "A Rapid Technique For The Purification Of Human Urinary CSF", *Exp. Hemat.*, 12:434, Abs. 195, (1984).

Waheed et al., "Purification of Colony–Stimulating Factor by Affinity Chromatography", *Blood*, 60:238 (1982).

Wang et al., "Purification of a Human Urinary Colony–Stimulating Factor", *J. Cell. Biochem.*, 21:263 (1983).

Wing et al., "Effect of Colony Stimulating Factor on Murine Macrophages", *J. Clin. Invest.*, 69:270 (1982).

Wong et al., "Human GM–CSF: Molecular Cloning of the Complementary DNA and Purification of the Natural and Recombinant Proteins", *Science*, 228:810 (1985).

Wu et al., "Purification of a Colony–stimulating Factor from Cultured Pancreatic Carcinoma Cells", *J. Biol. Chem.*, 254:6226 (1979).

Wu et al., "Granlocyte and Macrophage Colony Stimulating Factor From Human Placenta Conditioned Medium", *Biochem.*, 19:3846 (1980).

Yokota et al., "Isolation and characterization of a mouse cDNA clone that expresses mast–cell growth–factor activity in monkey cells", *PNAS(USA)*, 81:1070 (1984).

Fig. 1a  Human N-terminal:

```
1               5                   10                  15
Glu-Glu-Val-Ser-Glu-Tyr-Cys-Ser-His-Met-Ile-Gly-Ser-Gly-His 20                  25                  30
Leu-Gln-Ser-Leu-Gln-Arg-Leu-Ile-Asp-Ser-Gln-Met-Glu-Thr-Ser 35                  40
Cys-Gln-Ile-Thr-Phe-Glu-Phe-Val-Asp-Gln-Glu-Gln-Leu
```

Fig. 1b  Murine N-terminal:

```
1               5                   10                  15
Lys-Glu-Val-Ser-Glu-His-Cys-Ser-His-Met-Ile-Gly-Asn-Gly-His- 20                  25                  30
Leu-Lys-Val-Leu-Gln-Gln-Leu-Ile-Asp-Ser-Gln-Met-Glu-Thr-Ser- 35
(Tyr-Gly-Ile-Ala-Phe-Glu- X -Val-Thr)
```

Fig. 1c  Murine internal cyanogen bromide-cleavage peptide:

```
1               5                       10
[Met]-(Arg)-Phe-Lys-Asp-Asn-Thr-Pro-Asn-Ala-Phe-Ala-Asp-Glu- 15              20
Arg-Leu-Gln-Glu-Asp-Ser-Asn-Asn-Leu-Asn
```

FIG. 1

Human CSF AA Sequence & Oligos

```
NH2+
GLU  GLU  VAL  SER  GLU  TYR  CYS  SER  HIS  MET  ILE  GLY

5'+
GAG  GAG  GTG  TCC  GAG  TAC  TGC  TCC  CAC  ATG  ATC  GGC
 A    A    C    T    A    T    T    T    T         T    G
           T    A                        A         A    T
           A    G                        G              A
                AGC                      AGC
                 T                        T
```

EK12
```
 CC  GAT  CAT  GTG  GGA  GCA  GTA  CTC
  A              A         A         T
```

EK13
```
 CC  GAT  CAT  GTG  GCT  GCA  GTA  CTC
  A              A         A    A    T
```

EK14
```
 CC  GAT  CAT  GTG  GGA  GCA  GTA  CTC  GGA  CAC  CTC  CTC
                     CT                   CT
```

EK15
```
GAG  TAC  TGC  TCC  CAC  ATG
 A    T    T   AG    T
```

EK18  GAG  GAG  GTG  TCC  GAG  TAC
```
       A    A    C   AG    A    T
```

EK21  GTA  CTC  GGA  CAC  CTC  CTC
```
       A    T    A    G    T    T
```

EK22  GTA  CTC  GCT  CAC  CTC  CTC
```
       A    T    A    G    T    T
```

EK23  GAG  TAC  TGC  TCC  CAC  ATG  ATC  GG
```
       A    T    T    T    T         T
                      A
                      G
```

EK24  GAG  TAC  TGC  AGC  CAC  ATG  ATC  GG
```
       A    T    T    T    T         T
```

FIG. 3

PURIFIED HUMAN CSF-1

The present application is a Continuation of U.S. application Ser. No. 07/913,266, filed Jul. 14, 1992, now abandoned, which is a continuation of application Ser. No. 07/607,230, filed Oct. 31, 1990, now abandoned, which is a continuation of application Ser. No. 07/286,304, filed Dec. 16, 1988, now abandoned, which is a continuation of application Ser. No. 07/002,400 filed Dec. 3, 1986, now abandoned, and which corresponds to international application No. PCT/US86/00251, filed Feb. 5, 1986, which in turn is a continuation-in-part of application Ser. No. 06/698,358, filed Feb. 5, 1985, now abandoned.

TECHNICAL FIELD

The present invention relates to the purification of proteins, to the products of such purification, and to DNA probes constructed therefrom. More specifically, the invention relates to the purification and sequencing of murine and human colony stimulating factor-1 (CSF-1).

BACKGROUND ART

The ability of certain factors produced in very low concentration in a variety of tissues to stimulate the growth and development of bone marrow progenitor cells into granulocytes and/or macrophages has been known for nearly 15 years. The presence of such factors in sera, urine samples, and tissue extracts from a number of species is demonstrable using an in vitro assay which measures the stimulation of colony formation by bone marrow cells plated in semi-solid culture medium. There is no known in vivo assay. Because these factors induce the formation of such colonies, the factors collectively have been called Colony Stimulating Factors (CSF).

More recently, it has been shown that there are at least four subclasses of human CSF proteins which can be defined according to the types of cells found in the resultant colonies. One subclass, CSF-1 results in colonies containing macrophages predominantly. Other subclasses produce colonies which contain both neutrophilic granulocytes and macrophages; which contain exclusively neutrophilic granulocytes; and which contain neutrophilic and eosinophilic granulocytes and macrophages.

There are murine factors analogous to the first three of the above human CSFs. In addition, a murine factor called IL-3 induces colonies from murine bone marrow cells which contain all these cell types plus megakaryocytes, erythrocytes, and mast cells, in various combinations. These CSFs have been reviewed by Dexter, T. M., *Nature* (1984) 309:746, and Vadas, M. A., et al. *J Immunol* (1983) 130:793.

The invention herein is concerned with the purification of proteins which are members of the first of these subclasses, CSF-1. This subclass has been further characterized and delineated by specific radioimmunoassays and radioreceptor assays—e.g., antibodies raised against purified CSF-1 are able to suppress specifically CSF-1 activity, without affecting the biological activities of the other subclasses, and macrophage cell line J774 contains receptors which bind CSF-1 specifically. A description of these assays was published by Das, S. K., et al, *Blood* (1981) 58:630.

Purification methods for various CSF proteins have been published.

Stanley, E. R., et al. *J Biol Chem* (1977) 252:4305 reported purification of a CSF protein from murine L929 cells to a specific activity of about $1\times10^8$ units/mg, which also stimulated mainly macrophage production. Waheed, A., et al. *Blood* (1982) 60:238 described the purification of mouse L-cell CSF-1 to apparent homogeneity using a rabbit antibody column and reported the first 25 amino acids of the murine sequence (Ben-Avram, C. M., et al. *Proc Natl Acad Sci (USA)* (1985) 882:4486.

Stanley, E. R., et al. *J Biol Chem* (1977) 252:4305–4312 disclosed a purification procedure for CSF-1 from human urine and Das, S. K., et al. *Blood* (1981) 58:630: *J Biol Chem* (1982) 257:13679 obtained a human urinary CSF-1 at a specific activity of $5\times10^7$ units/mg which produced only macrophage colonies, and outlined the relationship of glycosylation of the CSF-1 proteins prepared from cultured mouse L-cells and from human urine to their activities. Wang, F. F., et al. *J Cell Biochem* (1983) 21:263, isolated human urinary CSF-1 to specific activity of $10^8$ U/mg. Waheed, A., et al. disclosed purification of human urinary CSF-1 to a specific activity of $0.7$–$2.3\times10^7$ U/mg on a rabbit antibody column (*Exp Hemat* (1984) 12:434).

Wu, M., et al. *J Biol Chem* (1979) 254:6226 reported the preparation of a CSF protein from cultured human pancreatic carcinoma (MIAPaCa) cells which resulted in the growth of murine granulocytic and macrophagic colonies. The resulting protein had a specific activity of approximately $7\times10^7$ units/mg.

Partially purified preparations of various CSFs have also been reported from human and mouse lung-cell conditioned media (Fojo, S. S., et al. *Biochemistry* (1978) 17:3109: Burgess, A. W., et al. *J Biol Chem* (1977) 252:1998); from human T-lymphoblast cells (Lusis, A. J., et al. *Blood* (1981) 57:13; U.S. Pat. No. 4,438,032); from human placental conditioned medium to apparent homogeneity and specific activity of $7\times10^7$ U/mg (Wu, M., et al. *Biochemistry* (1980) 19:3846).

Copending U.S. application Ser. No. 698,358 now abandoned describes cloning and expression of human and murine CSF-1 through recombinant techniques. A CSF protein of a different subclass, murine and human GM-CSF has been purified and the cDNAs cloned. This protein was shown to be distinct from other CSFs, e.g., CSF-1, by Gough, et al. *Nature* (1984) 309:763–767. Murine IL-3 has been cloned by Fung, M. C., et al. *Nature* (1984) 307:233. See also Yokota, T., et al. *PNAS* (1984) 81:1070–1074 Wong, G. G., et al. *Science* (1985) 228:810–815; Lee, F., et al. *PNAS* (1985) 82:4360–4364; and Cantrell, M. A., et al. *PNAS* (1985) 82:6250–6254.

DISCLOSURE OF THE INVENTION

In one aspect, the present invention relates to purified native human and murine CSF-1 proteins having the primary amino acid sequence as determined by the invention and to methods to obtain quantities of such protein and such sequence information. Refinements in purification techniques and careful sequencing have made possible identification of N-terminal sequences of both human and murine forms. This permits construction of probes useful in analyzing disease states, and in assessing changes in CSF-1 protein associated with these disease states. The probes are also useful as tools in obtaining DNA encoding CSF-1 for use in devising recombinant production of CSF-1 protein. Thus, in another aspect, the invention relates to probes designed on the basis of the determined sequences.

In one aspect, the invention relates to improved methods to purify CSF-1 from vertebrates. These methods include use of immunoaffinity chromatography to effect an efficient specific purification step followed by the use of reverse phase HPLC to assure freedom from contaminants. Monoclonal antibodies may be used in the immunoaffinity chromatography step. In another aspect, the invention relates to the native purified CSF-1 obtained, and to the DNA probes designed on the basis of the amino acid sequence determined from the purified material.

BRIEF DESCRIPTION OF THE DRAWINGS

FIGS. 1A, 1B and 1C show the partial amino acid sequences of human urinary and MIAPaCa, and murine L-929 cell CSF-1 as determined from purified native proteins.

FIG. 3 shows the sequence of oligomer probes designed from the amino acid sequence of human CSF-1.

MODES FOR CARRYING OUT THE INVENTION

A. Definitions

Figure 2:
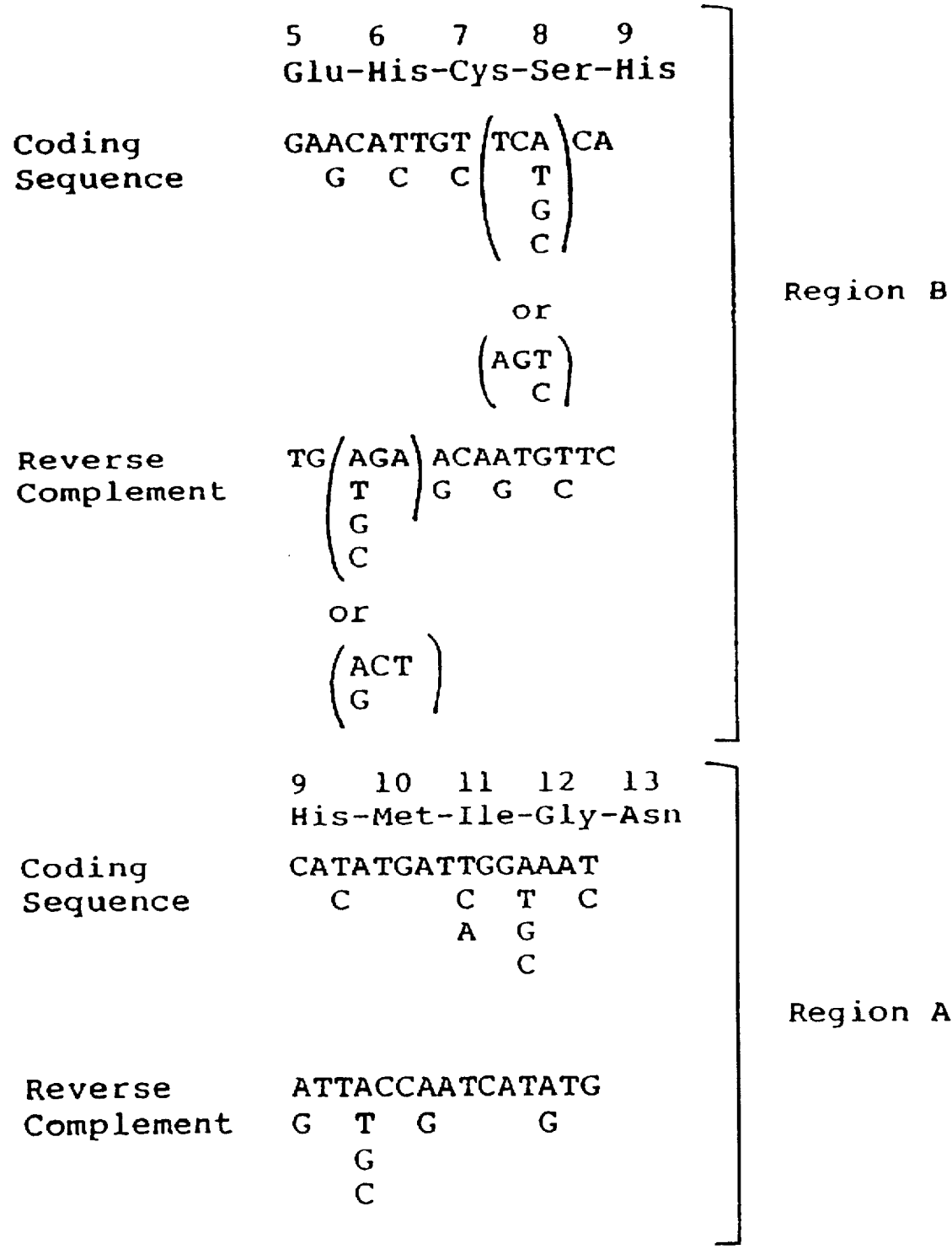
FIG. 2 shows the sequence of oligomer probes designed from the amino acid sequence of murine CSF-1.

"Colony stimulating factor-1 (CSF-1)" refers to a protein which exhibits the spectrum of activity understood in the art for CSF-1—i.e., when applied to the standard in vitro colony stimulating assay of Metcalf, D., *J Cell Physiol* (1970) 76:89, it results in the formation of primarily macrophage colonies. This factor is also active in the bone marrow proliferation assays of Moore, R. N., et al, *J Immunol* (1983) 131:2374, and of Prystowsky, M. B., et al. *Am J Pathol* (1984) 114:149. This protein may be isolated from any vertebrate species, preferably mammalian species, and most preferably human or murine subjects. There appears to be some species specificity: Human CSF-1 is operative both on human and on murine bone marrow cells; murine CSF-1 does not show activity with human cells. Therefore, human CSF-1 should be positive in the specific murine radioreceptor assay of Das, S. K., et al. *Blood* (1981) 58:630, and the biological activity of the human protein is inhibited by neutralizing antiserum to human urinary CSF-1 (Das, S. K., et al. supra).

Certain other properties of CSF-1 have been recognized more recently, including the ability of this protein to stimulate the secretion of series E prostaglandins, interleukin-1, and interferon from mature macrophages (Moore, R., et al. *Science* (1984) 223:178) and other effects on monocytes as described below. The mechanism for these latter activities is not at present understood, and for purposes of definition herein, the criterion for fulfillment of the definition resides in the ability to stimulate the formation of monocyte/macrophage colonies using bone marrow cells from the appropriate species as starting materials. (It is known that the proliferative effect of CSF-1 is restricted to cells of mononuclear phagocytic lineage (Stanley, E. R., *The Lymphokines* (1981), Stewart, W. E., II, et al. ed. Humana Press, Clifton, N.J.), pp. 102–132) and that receptors for CSF-1 are restricted to these cell lines (Byrne, P. V., et al. *Cell Biol* (1981) 91:848)).

As is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Further, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Indeed, native human urinary CSF-1 is isolated as a highly glycosylated dimer of 45 kd. Certain aspects of such augmentation are accomplished through post-translational processing systems of the producing host; other such modification may be introduced in vitro. In any event, the subject protein is within the definition of CSF-1 regardless of its state of aggregation or derivatization so long as the activity of the protein, as defined above, is present. It is expected, of course, that such modifications may quantitatively or qualitatively affect the activity, either by enhancing or diminishing the activity of the protein in various assays.

Further, individual amino acid residues in the chain may be modified by oxidation, reduction or other derivatization at the protein level, or the protein may be cleaved to obtain active fragments. Such alterations which do not destroy activity are included in the definition. Of course, the CSF-1 derived from different vertebrate species is not expected to exhibit complete homology, and these variations are included in the definition.

B. Utility

The CSF-1 proteins of the invention are capable both of stimulating monocyte-precursor/macrophage cell production from progenitor marrow cells, thus enhancing the effectiveness of the immune system, and of stimulating such functions of these differentiated cells as the secretion of lymphokines in the mature macrophages.

In one application, these proteins are useful as adjuncts to chemotherapy. It is well understood that chemotherapeutic treatment results in suppression of the immune system. Often, although successful in destroying the tumor cells against which they are directed, chemotherapeutic treatments result in the death of the subject due to this side effect of the chemotoxic agents on the cells of the immune system. Administration of CSF-1 to such patients, because of the ability of CSF-1 to mediate and enhance the growth and differentiation of bone marrow-derived precursors into macrophages, results in a restimulation of the immune system to prevent this side effect, and thus to prevent the propensity of the patient to succumb to secondary infection. Other patients who would be helped by such treatment include those being treated for leukemia through bone marrow transplants; they are often in an immunosuppressed state to prevent rejection. For these patients also, the immunosuppression could be reversed by administration of CSF-1.

In general, any subject suffering from immunosuppression whether due to chemotherapy, bone marrow transplantation, or other, accidental forms of immunosuppression such as disease (e.g., acquired immune deficiency syndrome) would benefit from the availability of CSF-1 for pharmacological use. In addition, subjects could be supplied enhanced amounts of previously differentiated macrophages to supplement those of the indigenous system, which macrophages are produced by in vitro culture of bone marrow or other suitable preparations treated with CSF-1. These preparations include those of the patient's own blood monocytes, which can be so cultured and returned for local or systemic therapy.

The ability of CSF-1 to stimulate production of lymphokines by macrophages also makes CSF-1 directly useful in treatment of neoplasms and infections.

CSF-1 stimulates the production of interferons by murine-derived macrophage (Fleit, H. B., et al. *J Cell Physiol* (1981) 108:347, and human, partially purified, CSF-1 from MIA-PaCa cells stimulates the poly IC-induced production of interferon and TNF from human monocytes as illustrated below. In addition, CSF-1 stimulates the production of myeloid CSF by human blood monocytes.

Also illustrated below is a demonstration of the ability of murine CSF-1 (from L-cell-conditioned medium) to stimulate normal C3H/HeN mouse peritoneal macrophages to kill murine sarcoma TU5 targets. This activity is most effective when the CSF-1 is used as pretreatment and during the effector phase. The ability of CSF-1 to do so is much greater than that exhibited by other colony stimulating factors. In addition, the ability of murine cells to attack viruses is enhanced by CSF-1.

(Murine CSF-1 is inconsistently reported to stimulate murine macrophage to be cytostatic to P815 tumor cells (Wing, E. J., et al. *J Clin Invest* (1982) 69:270) or not kill other leukemia targets (Ralph, P. et al. *Cell Immunol* (1983) 76:10). Nogawa, R. T., et al. *Cell Immunol* (1980) 53:116, report that CSF-1 may stimulate macrophage to ingest and kill yeast.)

Thus, in addition to overcoming immunosuppression per se, CSF-1 can be used to destroy the invading organisms or malignant cells indirectly by stimulation of macrophage secretions and activity.

The CSF-1 of the invention may be formulated in conventional ways standard in the art for the administration of protein substances. Administration by injection is preferred; formulations include solutions or suspensions, emulsions, or solid composition for reconstitution into injectables. Suitable excipients include, for example, Ringer's solution, Hank's solution, water, saline, glycerol, dextrose solutions, and the like. In addition, the CSF-1 of the invention may be preincubated with preparations of cells in order to stimulate appropriate responses, and either the entire preparation or the supernatant therefrom introduced into the subject. As shown hereinbelow, the materials produced in response to CSF-1 stimulation by various types of blood cells are effective against desired targets, and the properties of these blood cells themselves to attack invading viruses or neoplasms may be enhanced. The subject's own cells may be withdrawn and used in this way, or, for example, monocytes or lymphocytes from another compatible individual employed in the incubation.

Although the existence of a pattern of activity designated CSF-1 has been known for some time, sufficient amounts of the protein responsible have never been obtained in sufficiently pure form to permit sequence determination, thus the construction of DNA probes to study disease states based on their associated nucleic acid patterns for lymphokine encoding materials has not been possible. The present invention provides sufficient sequence information so that probes can be constructed. Through a variety of additional purification procedures, sufficient pure CSF-1 has been obtained from human urine, from MIAPaCa cells and from murine L-cells cells to provide some amino acid sequence, thus permitting the construction of DNA oligomeric probes. The probes are useful in obtaining the coding sequence for the entire protein, as well as for assessing disease states. The purified protein, of course, is also useful therapeutically as described above, and for the production of antibodies for diagnostic and therapeutic use.

C. Purification

The CSF-1 proteins of the invention were purified in sufficient homogeneity and quantity to obtain N-terminal sequence in several ways.

As illustrated below, human urinary CSF-1 was partially purified by standard methods as described by Das, S. K., et al. *Blood* (1981) 58:630, followed by an affinity purification step using a rat monoclonal antibody to murine CSF-1, designated YYG106, attached to a SEPHAROSE B column (Stanley, E. R., *Methods Enzymol* (1985) 116:564) SEPHAROSE is a trademark for beaded agarose. The final step in purification was reverse phase HPLC in a 0.1% TFA/30% acetonitrile—0.1% TFA/60% acetonitrile buffer system.

For MIAPaCa CSF-1, which was produced serum-free by induction with phorbol myristic acetate, the cell supernatant was subjected to calcium phosphate gel chromatography (according to Das (supra)), followed by affinity chromatography using lentil lectin (in place of the ConA affinity step of Das), and then to the immunoaffinity step employing the YYG106 monoclonal antibody conjugated to SEPHAROSE B and to the reverse phase HPLC.

Murine CSF-1 was initially purified as described by Stanley, E. R., et al. *J Immunol Meth* (1981) 42:253–284 followed by the immune affinity column as described above for the human protein and then by reverse phase HPLC. Murine CSF-1 was also prepared in a truncated procedure using calcium phosphate chromatography directly on the L-cell supernatant and then the aforementioned affinity chromatography, followed by reverse phase HPLC.

In general, purification procedures for CSF-1 protein are particularly effective which utilize an immunoaffinity chromatography step, preferably, an immunoaffinity step employing a monoclonal antibody preparation, followed by reverse phase HPLC. The proteins may also be further analyzed using SDS-PAGE.

Immunoaffinity chromatography involves the use of standard methods, whereby the antibody preparation is supported on a suitable polymer support such as SEPHAROSE, dextran, or polyacrylamide, employing procedures appropriate to the nature of the support. Polyclonal antibody preparations for use in this step are prepared by immunizing a subject, preferably a mammalian subject, such as a rabbit, mouse, or rat with the purified protein, such as that derived from human urine or murine L-cell medium. The antiserum may be used directly as a polyclonal composition, or the spleen cells or peripheral blood lymphocytes of the immunized subject may be immortalized using, for example, the fusion procedure of Kohler and Milstein. The successfully fused cells are then screened for production of antibodies against CSF-1 to obtain a monoclonal antibody producing line. Monoclonal preparations are, of course, preferred, as a consistent composition is more easily obtained. A particularly preferred monoclonal antibody is that produced by the YYG106 cell line, which is a fusion between a rat myeloma line and spleen cells from a rat immunized with murine L-cell CSF-1.

For reverse phase HPLC, standard techniques are also employed. Any hydrophobic column, such as an alkyl-, aryl-, alkylaryl-, or arylalkyl derivatized support, for example phenyl SEPHAROSE or phenyl TSK may be used. The elution gradient depends on the choice of support.

Amino acid composition determination and sequencing were done by standard procedures, however the procedures were adapted to the specific problems presented by the proteins available, as further described below.

D. Probe Construction

Using the sequence information obtained from the purified proteins above, oligomeric DNA sequences were constructed using standard, commercially available techniques. Codon redundancy is accounted for by using mixtures of probes, or by using limited numbers of particular oligomers which include codons favored in mammalian expression.

E. Examples

The following examples are intended to illustrate but not to limit the invention.

E.1. Purification of Native Human CSF-1

Human urinary CSF-1 was partially purified by standard methods as described by Das, S. K., et al. *Blood* (1981) 58:630, followed by an affinity purification step using a rat monoclonal antibody to murine CSF-1, designated YYG106, attached to a SEPHAROSE B column (Stanley, E. R., *Methods Enzymol* (1985) 116:564). The final step in purification was reverse phase HPLC in a 0.1% TFA/30% acetonitrile—0.1% TFA/60% acetonitrile buffer system.

For MIAPaCa CSF-1, which was produced serum-free by induction with phorbol myristic acetate, the cell supernatant was subjected to calcium phosphate gel chromatography (according to Das (supra)), followed by affinity chromatography using lentil lectin (in place of the ConA affinity step of Das), and then to the immunoaffinity step employing the YYG106 monoclonal antibody conjugated to SEPHAROSE B and to the reverse phase HPLC, both as above described.

The urinary and MIAPaCa proteins, having been purified to homogeneity, were subjected to amino acid sequencing using Edman degradation on an automated sequencer. Sufficient N-terminal sequence of human CSF was determined (FIG. 1A) to permit construction of the probes shown in FIG. 3.

In more detail, for both MIAPaCa and urinary CSF-1, all buffers used contain 3 mM $NaN_3$ and 0.01 g/l PEG-6000. The initial step in each case is DEAE cellulose chromatography. About 100 l of pooled urine or an amount of MIAPaCa medium containing a comparable amount of CSF-1 activity are adjusted to pH 7.4 and dialyzed to remove salts. The dialyzate is then applied to a DEAE cellulose column (200 g dry weight, Eastman) preequilibrated in 30 mM Tris-HCl buffer, pH 7.4.

The column is washed with 40 mM NaCl in the same buffer, and eluted with the same buffer containing 250 mM NaCl. The fractions containing CSF-1, as analyzed by the bone marrow proliferation assay, are dialyzed or ultrafiltered to remove ions. The deionized eluate is then treated with calcium phosphate gel (58 ml/g protein) and the gel is washed twice by decantation with 10 l of 5 mM sodium phosphate buffer, pH 6.5. The slurry is resuspended in 2.5 l and adjusted to 25 mM sodium phosphate buffer, pH 6.5 to elute the CSF-1, which is separated from the gel by centrifugation at 12,000×g for 10 min and concentrated to 50 ml for further DEAE cellulose chromatography.

The eluted CSF-1 in 100 mM Tris-HCl buffer, pH 7.4 is then applied to a DEAE cellulose column preequilibrated with the same buffer and eluted with a linear gradient of NaCl (0–150 mM) in the same buffer. The CSF-1 elutes at approximately 75–130 mM NaCl, and these fractions are dialyzed and concentrated to 15 ml for affinity chromatography on ConA SEPHAROSE.

The concentrate is dissolved in 100 mM acetate, 1M NaCl, 10 mM $MgCl_2$, 10 mM $CaCl_2$, 10 mM $MnCl_2$, pH 6.0 (ConA buffer) and applied to a ConA SEPHAROSE column (Pharmacia). The column is washed with ConA buffer at 4° C. and then eluted with 100 mM α-methyl-D-glucoside in the same buffer and the fractions containing CSF-1, as determined by the bone marrow proliferation assay, are pooled and concentrated to 3 ml for gel filtration.

The CSF-1 is taken up in 30 mM Tris-HCl, pH 7.4 and applied to a BIO-GEL™ P-100 column equilibrated in the same buffer (BIO-GEL™ P gels are porous polyacrylamide beads prepared by copolymerization of acrylamide and N,N'-methylene-bis-acrylamide, BioRad Labs, Rockville Center, N.Y.). The active fractions elute during the void volume and are pooled and dialyzed against 50 mM phosphate, pH 6.5.

The pooled eluate from the gel filtration step is then subjected to immunosorbent chromatography using $10^5$ U CSF-1 for each ml of a PABAE-Seph-4B column derivatized to anti-CSF-1 monoclonal antibody, prepared as described in the following paragraph.

(The column was prepared using the monoclonal antibody YYG106 which is produced from a hybridoma maintained in suspension culture of 10% FCS-α medium. The hybridoma was obtained by fusion between spleen cells from a rat immunized with partially purified murine L-cell CSF-1 and a rat myeloma line. Serum-free medium for the production of the desired monoclonal antibody is prepared by culturing washed cells ($10^5$/ml) in HB101 medium (Hana Biologics, Berkeley, Calif.) and harvesting the medium by centrifugation at 400×g for 15 min at 4° C. from cultures in which cell viability has dropped to 25%. The recovered medium is then brought to 50% saturation with ammonium sulfate and the precipitate collected by centrifugation at 1200 g for 15 min at 4° C. dialyzed against 20 mM sodium phosphate buffer, pH 7.1 and applied to a DEAE AFFI-GEL Blue (BioRad Labs, Rockville Center, N.Y. DEAE AFFI-GEL™ blue gel is a bifunctional affinity gel containing Cibacron blue F3GA dye covalently attached to DEAE BIO-GEL™ A agarose gel column equilibrated in the same buffer at 4° C. The column is then washed with 20 mM sodium phosphate buffer, pH 7.1 and the desired monoclonal antibody eluted with a 0–0.15M NaCl gradient in this buffer. The antibody activity of the fractions is determined and the active fractions pooled and concentrated by ultrafiltration.

A packed bed volume of PABAE-Seph (SEPHAROSE 4B derivatized with p-aminobenzamidoethyl-) is washed in 0.5M HCl (cold) and treated with 0.2M $NaNO_2$ incubated on ice for 7 min. The gel is washed 3 times with at least 2 volumes of ice cold distilled water and equal volumes of washed gel and concentrated monoclonal antibody (3 mg/ml in 0.2M sodium borate buffer, pH 8.0) are mixed and rocked for 16 hr at 4° C. The resulting derivatized PABAE-Seph-4B is then washed sequentially with 5 volumes of 1% triethanolamine in 50 mM Tris-HCl, pH 8.5, 5 volumes of 6M urea in 0.1M Tris-HCl, pH 7.4 and 5 volumes of 0.4M sodium bicarbonate prior to equilibration in 0.05M sodium phosphate buffer, pH 6.5.)

The pooled gel filtration eluate as described above is treated with the PABAE-Seph-4B-antibody derivatized column at $10^5$ U/ml at 4° C. and recycled through the column. The column is washed with 50 mM sodium phosphate buffer, pH 6.5, then with 100 mM glycine-HCl, pH 2.0 prior to elution using 4M KSCN, and then 0.1M glycine-HCl, pH 2.0, which eluates are collected in a vessel containing 0.6 column volumes of 1M ammonium bicarbonate. The eluates are separately dialyzed against 0.01 g/l PEG-6000.

The resulting human urinary CSF-1 has a specific activity of approximately $8 \times 10^7$ U/mg.

The human urinary or MIAPaCa CSF-1 is then subjected to reverse phase HPLC using 0.1% TFA/acetonitrile gradient as described above.

For some MIAPaCa preparations, derived from serum-free medium, the purification is accomplished using the calcium phosphate gel filtration step as described above, followed by affinity chromatography using lentil lectin in place of ConA, but otherwise as described above, followed by the immunoabsorbant chromatography and HPLC steps described.

SDS-gel electrophoresis of the HPLC eluates confirms homogeneity for both human urinary and MIAPaCa preparations. The human urinary CSF-1 migrated as species having apparent molecular weights ranging from 61,000 to 98,000 daltons ±10% on SDS-PAGE under non-reducing conditions and as species having apparent molecular weights ranging form 29,000 to 54,000 daltons ±10% on SDS-PAGE under reducing conditions, with bands at 29,000, 32,000, 46,000 and 54,000 daltons.

Construction of Probes

Sufficient N-terminal sequence of human CSF was determined to permit construction of probes as shown in FIG. 3. The N-terminal sequences of the purified MIAPaCa and urinary CSF-1 are identical. The resulting synthetic oligonucleotides are useful for diagnosis and determining the etiology of various disease states in humans.

E.2. Murine CSF-1

Protein Purification

Murine CSF-1 can be purified by standard methods similar to those that are disclosed by Stanley, E. R., et al. *J Biol Chem* (1977) 252:4305; Stanley, E. R., et al. *J Immunol Meth* (1981) 42:253–284 and by Wang, F. F. et al. *J Cell Biochem* (1983) 21:263–275. In the alternative, the batch calcium phosphate gel chromatography step (Stanley, E. R., *J Immun Meth* (supra) can be directly followed by immunoaffinity chromatography.

In more detail, the initial preparation of serum-free L cell conditioned medium is conducted as described by Stanley, E. R., et al *J Immunol Meth* (supra) and then subjected to calcium phosphate gel chromatography by adding calcium phosphate gel to 20–40 l of serum-free L-cell conditioned medium (40 ml/l medium) and the mixture is stirred at $-20°$ for 10 min before the gel is allowed to settle in repetitive batch treatments.

The eluates are then subjected to affinity chromatography using PABAE-Seph-4B with YYG106 antibodies as described above in connection with the human protein, except that $10^6$ U/ml is used, and the second elution step is omitted.

The thus purified murine material is subjected to reverse phase HPLC and elution with TFA/acetonitrile as described above. The specific activity of the purified murine material is about $4–8\times10^7$ U/mg.

Similar to the CSF-1 purified from humans, the purified murine CSF-1 is a heavily glycosylated dimer: the asparagine-linked complex type saccharides representing 40–60% of the molecular weight. Upon SDS-PAGE in the absence of 2-mercaptoethanol, the purified preparations had an apparent molecular weights of 70 and 90 kd and on reduction gave a major band at 40 kd and a minor band at 33 kd which were derived from dimers of parent molecular weights of 70 kd and 90 kd. It is clear that the 40 kd subunit is more highly glycosylated than the 33 kd subunit; also, the N-terminal sequences of both subunits are identical.

Overall composition data for the mouse protein were also obtained as shown below. These data show correct relative mole % for those amino acids showing good recoveries; however the numbers are not absolute, as histidine and cysteine were not recovered in good yield.

| Amino Acid | mole % | residues/125 |
|---|---|---|
| Asp | 20.1 | 25.1 |
| Glu | 20.0 | 25.0 |
| His | — | — |
| Ser | 6.0 | 7.5 |
| Thr | 5.9 | 7.4 |
| Gly | 5.4 | 6.8 |

-continued

| Amino Acid | mole % | residues/125 |
|---|---|---|
| Ala | 6.8 | 8.5 |
| Arg | 3.0 | 3.8 |
| Pro | 6.7 | 8.4 |
| Val | 5.3 | 6.6 |
| Met | 1.1 | 1.4 |
| Ile | 3.9 | 4.9 |
| Leu | 8.5 | 10.6 |
| Phe | 6.0 | 7.5 |
| Lys | 3.5 | 4.4 |
| Tyr | 4.1 | 5.1 |

The conversion to residues/125 was based on an approximation of sequence length from molecular weight.

Primary structure determination was conducted using automated Edman degradation equipment and analyzing the sequentially cleaved amino acids by reverse phase HPLC. Conventional sequencing resulted in the first 13 N-terminal amino acids. Because of the presence of methionine at position 10, and the limited number of methionine residues present, CNBr-digested protein was loaded onto the sequencer without prior fractionation of the fragments, and only 3 sequences were obtained. These were the expected N-terminal sequence, a sequence beginning Ile-Gly-Asn which overlapped the known N-terminal sequence; and a sequence beginning X-Phe-Lys at approximately 50% yield. The difference in amounts of the latter two fragments and the known sequence of the first permitted the determination of sequence in the three fragments simultaneously through a limited number of residues.

Sequence determination was then performed on a purified CNBr internal fragment. A contaminating fragment to this N-terminated Glu-Phe-Lys peptide was removed by treating with O-phthalaldehyde to block fragments which do not have proline at the N-terminus. (The internal sequence has proline at position 7.) The sequencing was continued, and the next residues of the internal fragment thus identified. The sequencing results are shown in FIG. 1B and 1C. The data are consistent with a dimeric protein containing two identical subunits and with release by CNBr of a peptide from both ends of a single subunit, these ends being residues 1-25 and the internal sequence, each with an approximate molecular weight of 2.5 kd.

The foregoing data represent approximately half of the CSF-1 sequence based on an unglycosylated subunit molecular weight of 14.5 kd. Since L-cell CSF-1 is about 60% carbohydrate by weight, and only one potential site of glycosylation (positions 37, 38, and 39) has been identified, the remainder of the molecule is heavily glycosylated.

Preparation of Probes

FIG. 2 shows a series of oligonucleotide probes complementary to murine CSF-1 prepared on the basis of the sequence information obtained. These are mixed probes to account for codon redundancy, or are designed to favor mammalian preference codons.

E.3. Biological Activity

Additional data relevant to the activity of CSF-1 was provided using partially purified MIAPaCa CSF-1 or murine L-cell CSF-1. CSF-1 was shown to enhance the production of interferon and tumor necrosis factor (TNF) by induced human monocytes by up to 10-fold. CSF-1 also was demonstrated to stimulate macrophage antitumor toxicity.

Stimulation of TNF Production by Human Monocytes

MIAPaCa CSF-1 was purified from the supernatant by calcium phosphate gel filtration and lentil lectin chromatography. For assay of lymphokine production, peripheral blood-adherent cells were incubated in duplicate flasks containing $10^7$ cells each. One flask was treated with 1000 U/ml CSF-1 purified as above. After 3 days, the cells were harvested, and washed, and resuspended at a cell concentration of $5\times10^5$/ml and plated in 24-well plates at 0.5 ml/well. The wells were treated with 10 μg/ml LPS and 20 ng/ml PMA for 48 hr and the supernatants were harvested for TNF assay. Cells treated with CSF showed TNF secretions approximately nine-fold higher than the untreated cells (1500 U/ml, compared to 162 U/ml).

Stimulation of Interferon Production by Human Monocytes

In an analogous experiment to determine the effect of CSF-1 on interferon production, peripheral blood-adherent cells were incubated for 3 days in the presence and absence of 1000 U/ml CSF-1, as described above, harvested, resuspended at $5\times10^5$/ml, and plated in a 25-well plate, as described above. The cells were induced for interferon production by addition of varying amounts of poly IC. The supernatants were assayed for interferon production by their cytopathic effect on VSV-infected GM 2504 cells. The CSF-1-stimulated cells showed production of 100 U/ml when induced with 50 μg/ml poly IC, as described by McCormick. F., et al. *Mol Cell Biol* (1984) 4:166, whereas comparably induced untreated cells produced less than 3 U/ml.

Stimulation of Myeloid CSF Production by Human Monocytes

Monocytes were incubated ± CSF-1 for 3 days and then induced for production of myeloid CSF as in Table 1. The three representative experiments shown, used blood from different donors.

TABLE 2

| Treatment | | Kill % | Increase Due to CSF-1 % |
|---|---|---|---|
| DAY 0→1 | DAY 1→3 | | |
| — | — | 13 | |
| — | LK | 39 | |
| — | CSF-1 + LK | 49 | 26 |
| CSF-1 | LK | 51 | 31 |
| CSF-1 | CSF-1 + LK | 60 | 54 |
| — | — | 3 | |
| — | LK | 35 | |
| — | CSF-1 + LK | 47 | 34 |
| CSF-1 | — | 7 | |
| CSF-1 | LK | 49 | 40 |
| CSF-1 | CSF-1 + LK | 69 | 97 |

Increase in the ability to kill the target cells was noted whether CSF-1 was added during the preliminary 1 day of growth or during the period of induction; however, the most dramatic effects were observed when CSF-1 was present during both of these periods.

The possibility of contaminating bacterial lipopolysaccharide (LPS) as the cause of stimulation of monocytes and macrophages was excluded: The LPS content of the applied CSF-1 was low (<0.3 ng/3000 U CSF-1, by Limulus amoebocyte lysate assay); activity was removed by application to an anti-CSF-1 column; polymyxin B was used to neutralize LPS; macrophages from C3H/HeJ mice respond to CSF-1 but do not respond to LPS.

TABLE 1

| | Myeloid CSF (U/ml) | | | | | |
|---|---|---|---|---|---|---|
| | Exp. 1 | | Exp. 2 | | Exp. 3 | |
| Induction | −CSF | +CSF | −CSF | +CSF | −CSF | +CSF |
| medium | 0 | 0 | 0 | 0 | 0 | 0 |
| 0.1 μg/ml LPS | — | — | 0 | 0 | 0 | 80 ± 17 |
| 1 μg/ml LPS | 0 | 700 ± 72 | 40 ± 20 | 200 ± 20 | 103 ± 12 | 377 ± 57 |
| 0.1 μg/ml LPS + 2 ng/ml PMA | — | — | 617 ± 50 | 993 ± 101 | 1120 ± 82 | 1280 ± 60 |
| 1 μg/ml LPS + 2 ng/ml PMA | 283 ± 42 | 983 ± 252 | 360 ± 92 | 1400 ± 180 | 537 ± 47 | 1080 ± 122 |
| 2 ng/ml PMA | — | 370 ± 17 | 297 ± 6 | 183 ± 15 | 380 ± 52 | 716 ± 76 |

Therefore, CSF-1 stimulates CSF-GM production.

Stimulation of Tumor Cell Killing by Murine Macrophage; Comparison to other Colony Stimulating Factors To assay macrophage stimulation, murine CSF-1 obtained from L-cell-conditioned medium, was used as a model for the recombinantly produced CSF-1 from pcCSF-17 in an assay which showed stimulation of the ability of murine macrophages to kill sarcoma targets. In this assay, normal 2 hr adherent C3H/HeN mouse peritoneal macrophages were incubated for 1 day in vitro with and without CSF-1 and then mixed at a 20:1 ratio with $^3$H-thymidine-labeled mouse sarcoma TU5 cells along with 10% v/v conA-induced (10 μg/ml) spleen lymphokine (LK), which contains gamma interferon. The release of labeled thymidine over the following 48 hr was used as a measure of tumor cell killing. The effect of adding CSF-1 as murine L-cell-conditioned medium containing 1200 U/ml CSF-1 is shown in the following table.

CSF-GM was prepared from 6 mouse lungs obtained 5 hours after IV administration of 5 μg LPS. The lungs were chopped and incubated for 3 days in serum free medium, and the supernatant was depleted of CSF-1 using a YYG106 affinity column (CSF-1 content reduced from 270 U/ml to 78 U/ml). CSF-G was prepared from similarly treated LDI serum fee medium. Both CSF-GM and CSF-G contents were assayed at 2000 U/ml by colony stimulating assay.

The peritoneal macrophages were incubated with 40% of either of the foregoing media or with L-cell medium assayed at 2000 U/ml CSF-1 for 1 day, and then incubated for 48 hours either with additional medium or with LK, and assayed for TU5 killing as described above.

The results are showed that while CSF-1 showed marked enhancement of toxicity to TU5, neither CSF-G nor CSF-GM had any effect.

Stimulation of Murine Antiviral Activity

Adherent murine thioglycolate-elicited macrophages were incubated with CSF-1 for 3 days and infected with VSV overnight. Polymyxin B was added to test samples to block the LPS induction of interferon. The following table shows crystal violet staining of cells remaining adherent.

TABLE 3

| Treatment | Crystal Violet | |
| --- | --- | --- |
| | −Polymyxin B (mean) (S.D.) | +Polymyxin B |
| Medium/No VSV | .158 + .019 | |
| Medium + VSV | .0583 + .02 | .049 + .009 |
| CSF-1625 U/ml + VSV | .139 + .018 | .177 + .04 |
| 1250 + VSV | .167 + .06 | .205 + .07 |
| 2500 + VSV | .160 + .06 | .219 + .04 |
| 5000 + VSV | .150 + .03 | .202 + .06 |

CSF-1 treated cells, therefore, showed protection of the macrophage against VSV.

E.4. Formulation of CSF-1

The recombinantly produced human CSF-1 may be formulated for administration using standard pharmaceutical procedures. Ordinarily CSF-1 will be prepared in injectable form, and may be used either as the sole active ingredient, or in combination with other proteins or other compounds having complementary or similar activity. Such other compounds may include alternate antitumor agents such as adriamycin, or lymphokines, such as IL-1, -2, and -3, alpha-, beta-, and gamma-interferons and tumor necrosis factor. The effect of the CSF-1 active ingredient may be augmented or improved by the presence of such additional components. As described above, the CSF-1 may interact in beneficial ways with appropriate blood cells, and the compositions of the invention therefore include incubation mixtures of such cells with CSF-1, optionally in the presence of additional lymphokines. Either the supernatant fractions of such incubation mixtures, or the entire mixture containing the cells as well may be used.

We claim:

1. Purified mature human CSF-1 protein characterized by the ability to stimulate bone marrow cells to form primarily macrophages with a specific activity of approximately $8 \times 10^7$ U/mg and further characterized by a single amino-terminal amino acid sequence comprising: Glu-Glu-Val-Ser-Glu-Tyr-Cys-Ser-His-Met-Ile-Gly, said protein further characterized by having (1) an apparent molecular weight in the range of 61,000 to 98,000 daltons±10% on SDS-PAGE under non-reducing conditions; and (2) an apparent molecular weight in the range of 29,000 to 54,000 daltons±10% on SDS-PAGE under reducing conditions.

2. The purified human CSF-1 protein of claim 1 which has upon N-terminal sequencing, a single N-terminal amino acid sequence comprising:

Glu-Glu-Val-Ser-Glu-Tyr-Cys-Ser-His-Met-Ile-Gly-Ser-Gly-His-Leu-Gln-Ser-Leu-Gln-Arg-Leu-Ile-Asp-Ser-Gln-Met-Glu-Thr-Ser-Cys-Gln-Ile-Thr-Phe-Glu-Phe-Val-Asp-Gln-Glu-Gln-Leu.

3. A composition comprising an amount of the purified human CSF-1 protein of claim 1 or 2 effective to stimulate monocyte precursor/macrophage cell production, and a physiologically suitable excipient.

* * * * *